(12) United States Patent
Miller et al.

(10) Patent No.: US 6,299,602 B1
(45) Date of Patent: Oct. 9, 2001

(54) APPARATUS AND METHOD FOR CATHETERIZATION OF BLOOD VESSELS

(75) Inventors: Larry S. Miller; Daniel P. Daigle, both of Baton Rouge, LA (US)

(73) Assignee: Scan, Inc., Gulfport, MS (US)

( * ) Notice: Subject to any disclaimer, the term of this patent is extended or adjusted under 35 U.S.C. 154(b) by 0 days.

(21) Appl. No.: 09/433,526

(22) Filed: Nov. 3, 1999

(51) Int. Cl.[7] .................................................. A61M 5/178
(52) U.S. Cl. ................................ 604/164.01; 604/165.01
(58) Field of Search ........................ 604/164.01, 164.02, 604/164.03, 164.08, 58, 164.12, 165.01, 165.02, 163, 171

(56) References Cited

U.S. PATENT DOCUMENTS

| | | | |
|---|---|---|---|
| 4,966,589 | 10/1990 | Kaufman | 604/174 |
| 4,976,698 | 12/1990 | Stokley | 604/174 |
| 5,007,901 | 4/1991 | Shields | 604/110 |
| 5,018,534 | 5/1991 | Grant | 128/877 |
| 5,041,097 | 8/1991 | Johnson | 604/167 |
| 5,186,712 | 2/1993 | Kelso et al. | 604/165 |
| 5,201,713 | 4/1993 | Rossetti | 604/165 |
| 5,215,525 | 6/1993 | Sturman | 604/164 |
| 5,376,071 | 12/1994 | Henderson | 604/53 |
| 5,562,634 | 10/1996 | Flumene et al. | 604/171 |
| 5,573,510 | 11/1996 | Isaacson | 604/158 |
| 5,971,959 | * 10/1999 | Liu | 604/164 |
| 6,200,294 | * 3/2001 | Liu | 604/198 |

* cited by examiner

Primary Examiner—Richard K. Seidel
Assistant Examiner—Kevin C. Sirmons
(74) Attorney, Agent, or Firm—Lowe Hauptman Gilman & Berner, LLP (57) ABSTRACT

A catheter insertion device is disclosed herein. The device allows an operator to insert a catheter within a vessel with a single hand enabling the operator to keep a grip on the patient's skin and vessel. The device also includes a needle tip sheath that protects operators from accidental needle punctures by contaminated needles.

25 Claims, 8 Drawing Sheets

APPARATUS AND METHOD FOR CATHETERIZATION OF BLOOD VESSELS

BACKGROUND OF THE INVENTION

1. Field of the Invention

This invention relates to medical catheters, more particularly to a catheter insertion device that protects users from accidental needle pricks, provides a gauge for multiple-attempt catheterizations, and provides a quick-taping system.

2. Prior Art

Administering intravenous medications and agents or installing intravenous monitoring devices requires the catheterization of veins or arteries (generally "vessels"). Intravenous catheters (usually flexible catheters) must be inserted into a vessel and must be positioned properly to establish and maintain the proper fluid flow through the catheter that remains in the vessel. One type of catheter insertion device comprises a needle and a plastic catheter tube that slides over the needle so that the needle point protrudes through the catheter. Introduction of the catheter into the vessel requires manipulation and positioning of the vessel as well as precise placement of the needle and catheter within the vessel. Once properly placed, the operator must carefully withdraw the needle and leave the catheter within the vessel.

Medical personnel ("operator") operate catheters as follows. The operator grips the posterior portion of the intravenous catheter with one hand and secures and holds the skin and vein of the patient with the other hand. The operator inserts and guides the needle tip through the patient's skin and into a vessel. Blood flows from the vessel through the passageway in the needle and into a catheter collection chamber. The operator advances the needle slightly to assure that the catheter has entered the vessel. The operator inserts the catheter into the vessel without advancing the needle. This additional insertion of the catheter is difficult and contributes to misstarts, which require the withdrawal and reinsertion of the intravenous catheter into the vessel. Thus, the patient may endure additional needle punctures.

With a majority of intravenous insertion attempts, operators must remove the hand that holds the patient's skin and vein and use that hand to remove the needle from the catheter. Because the operator is not gripping the patient's skin and vein, the catheter may slip from within the vessel and cause a misstart.

After removing the needle, the operator places it on a medical tray or hands it to an assistant. The removal and placement of the needles is usually done haphazardly because operators are focused on preventing withdrawal of the catheter from the vessel. Consequently, operators and assistants have been injured from needle pricks by contaminated needles. Thus, a need exists for a medical catheter that can minimize misstarts while at the same time preventing contaminated needles from injuring medical personnel.

ADVANTAGES AND OBJECTS OF THE INVENTION

The present invention has advantages over prior art devices. A protective sheath covers the needle tip when the needle has been removed from the catheter to prevent injuries to medical personnel. The design of the present device allows medical personnel to withdraw the needle from the catheter without moving the hand that holds the patient's skin and vessel. Therefore, the present invention decreases the risk of misstarts when withdrawing the needle from the catheter.

The present invention may be used in connection with a variety of intravenous catheters and needles, including catheters and needles of different sizes, lengths, and gauges. The catheter insertion device is constructed with a thumb ring that enables an operator to retract the catheter back to its starting point (when the locking member has not been engaged) after the catheter has been partially discharged using only a single hand. The present invention also incorporates a gauge positioned thereon to allow operators to safely identify the point at which it is safe and acceptable to return the device to a starting point. The present invention has an extended blood backflow chamber that allows multiple cannulation attempts without removing the catheter from a patient's tissue.

The present invention incorporates a fastening member that allows the catheter to be fixedly positioned (relative to the vessel in which the catheter has been positioned) within seconds after the catheter has successfully cannulated the blood vessel. A clamp may also be used to fluidly seal the catheter and prevent blood backflow from the vessel out through the catheter.

With the aforementioned considerations in mind, it is therefore an object of this invention to provide an intravenous catheter device that enables the operator to withdraw the needle using one hand without releasing the grip on the patient with the other hand.

It is a further object of the present invention to provide an intravenous catheter device that clamps and holds the catheter.

It is a further object of the present invention to provide an intravenous catheter device that can adapt to existing catheters and allow medical professionals to choose their own catheters.

It is a further object of the present invention to provide an intravenous catheter device that allows an operator to secure the catheter immediately after vessel catheterization without releasing the grip on the patient's arm.

These and other advantages and objects of this invention shall become apparent from the ensuing description of the invention.

SUMMARY OF THE INVENTION

The present invention is a catheter insertion device comprising: (a) a shaft having a first end and a catheter end, wherein the catheter end is configured to releasable engage a hollow catheter having a tip; (b) a sheath positioned on the shaft configured to have a passage therethrough and positioned to align the passage with a catheter; (c) a body slidably positioned on the shaft, attachable to a needle, and configured to align a needle with the passage in the sheath and with the catheter wherein the needle, the sheath, the shaft and the catheter are sized and spaced to position a needle tip of a needle beyond the catheter tip when the body is advanced toward the catheter end of the shaft, and to remove the needle tip from within the catheter and to position the needle tip within the passage of the sheath when the body is retracted toward the first end of the shaft.

The invention also comprises a method for intravenously inserting a catheter using the catheter insertion device. The method comprises the steps of (a) grasping the skin of a patient with one hand in the area of desired catheterization to fix the position of the skin and surrounding tissue relative to a vessel to be catheterized; (b) holding in the other hand the catheter insertion device; (c) inserting the needle and the catheter into the vessel until fluid flows from the vessel through the needle; and. (d) moving the catheter into the vessel to a desired position. The method also comprises the step of retracting the body until the needle tip is covered by the sheath.

BRIEF DESCRIPTION OF THE DRAWINGS

FIGS. 5a and 5b illustrate a fastening member used in connection with the present invention.

DETAILED DESCRIPTION OF THE PREFERRED EMBODIMENTS OF THE INVENTION

Illustrations of construction, design, and methods of operation of the invention are set forth below with specific references to the Figures. However, it is not the intention of the inventor that the scope of his invention be limited to these embodiments.

As used herein, "vertical" shall mean substantially along the y-axis shown in the Figures, while "horizontal" shall mean substantially along the x-axis shown in the Figures.

Figure 1A:
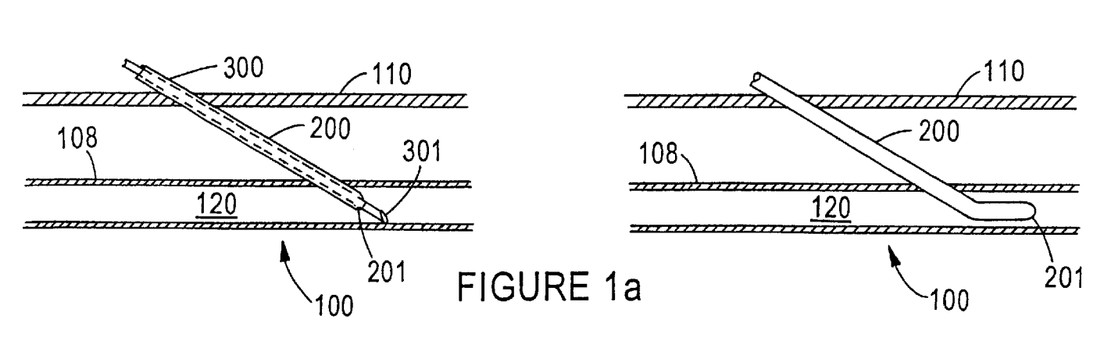
FIG. 1a is a side view of a correct placement of a catheter within the vessel lumen.
Figure 1B:
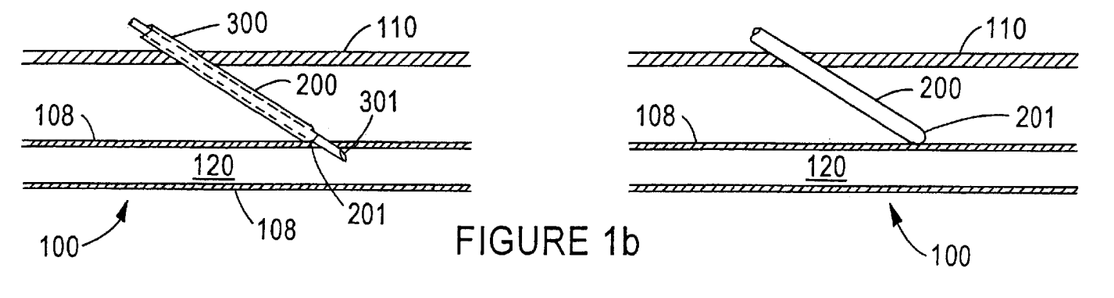
FIG. 1b is a side view of an erroneous placement of a catheter that does not initially penetrate a vessel.
Figure 1C:
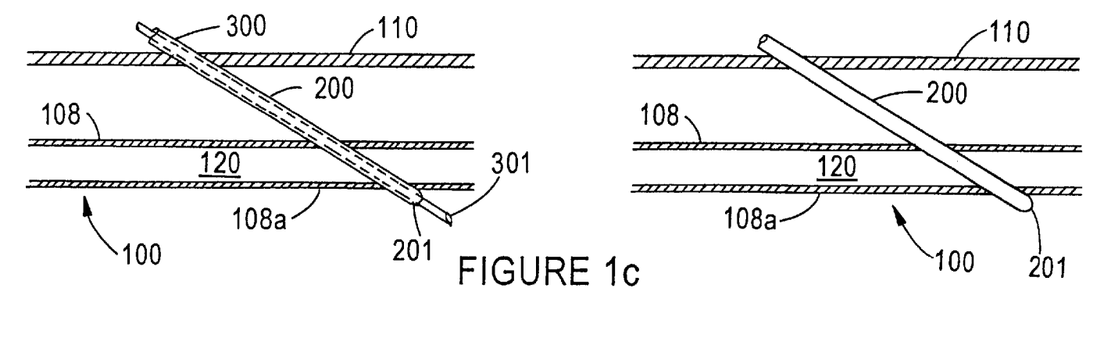
FIG. 1c is a side view of an erroneous placement of a catheter that penetrates completely through a vessel.

FIGS. 1a–1c illustrate various positions encountered during an attempted placement of catheter 200 within a vessel 100. FIG. 1a illustrates desired catheter 200 placement. The operator inserts catheter 200/needle 300 combination, with needle tip 301 protruding from catheter tip 201, inserted through vessel wall 108 into vessel lumen 120. To accomplish insertion, the operator prepares skin 110 with an antibacterial or sterilization agent. With one hand, the operator locates the vessel 100 to be catheterized and holds skin 110 and vessel 100 in a fixed position to prevent vessel 100 from moving when punctured. With the other hand, the operator advances the catheter 200/needle 300 combination by pushing it through skin 110 and advancing it until needle tip 301 enters the vessel lumen 120. The operator knows that needle 300 enters vessel 100 when he observes fluid entering chambers 233 (FIGS. 3a, 3b), 321 (FIG. 4) or needle head 320 (FIG. 7), or tubing connected thereto.

The next step is the most difficult and is where the majority of misstarts occur. As the operator advances catheter tip 201 into lumen 120 (and deeper into vessel 100) the operator removes needle 300. The operator advances catheter 200 until catheter hub 310 is against the exterior of the skin 110 or until there is a vessel obstruction that prevents further insertion. After an operator completes catheterization, he may connect catheter 200 to medication tubing, monitoring equipment, etc. at catheter hub 310.

The most difficult part of the procedure is successfully inserting catheter tip 201 into vessel 100. FIGS. 1b and 1c illustrate typical misstarts. In FIG. 1b, needle tip 301 advances into vessel 100. A backflow of blood is visible in collection chamber 321 indicating vessel puncture. However, catheter tip 201 is not within vessel lumen 120. Thus, when an operator removes needle 300, catheter 200 remains outside vessel wall 108, resulting in a misstart and requiring withdrawal and re-puncture of skin 110 and vessel 100.

FIG. 1c illustrates a similar problem. Both needle tip 301 and catheter tip 201 advance completely through vessel 100, leaving the catheter tip 201 outside lower vessel wall 108a. In this case, the operator observes fluid backflow when needle tip 301 enters vessel 100. However, the fluid backflow ceases when needle tip 301 exits the opposite side of vessel 100. This process is further complicated if the operator releases his grip on skin 110 and vessel 100 to handle needle 300 or catheter 200 with both hands. If an operator releases skin 110 before completion of the insertion, a properly placed catheter 200 will often shift position and exit vessel 100.

Figure 2A:
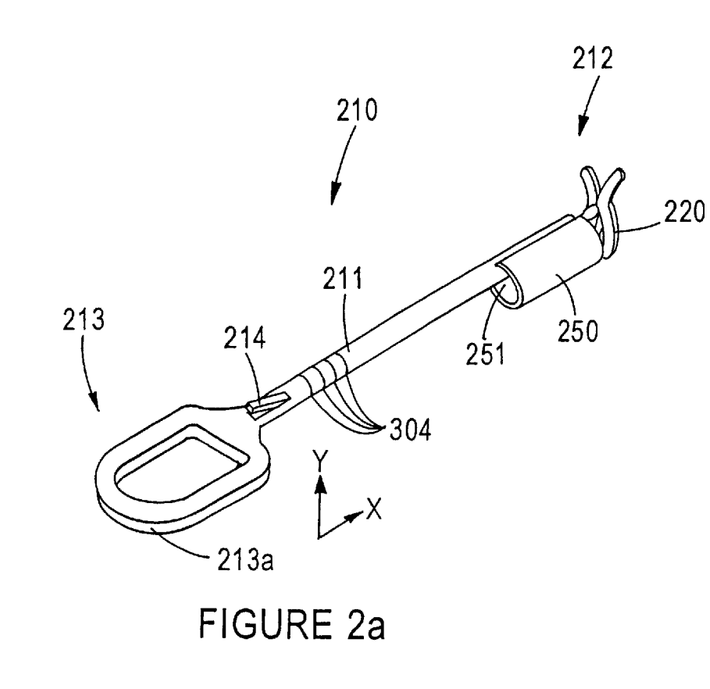
FIG. 2a illustrates an embodiment of a shaft used in connection with one embodiment of the present invention shown in FIGS. 3a–3c.

FIG. 2a illustrates the shaft 210 used in connection with the present invention. Shaft 210 comprises a first end 213 and a catheter end 212. First end 213 is preferably a ring 213a or other suitable shape to allow an operator to advance shaft 210, such as by using a thumb. Catheter end 212 may releasably engage a clip 220 (or clip 501 or 750 as described below).

Figure 2B:
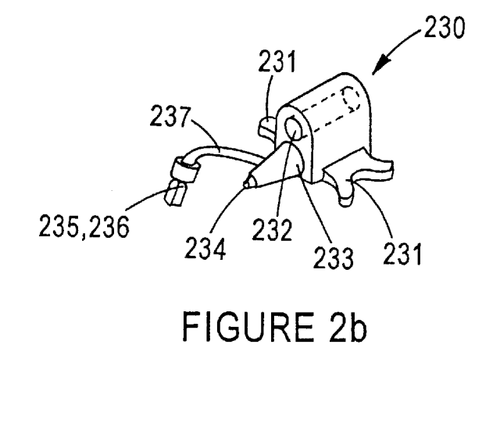
FIG. 2b illustrates an embodiment of a body used in connection with one embodiment of the present invention shown in FIGS. 3a–3c.

Shaft 210 has a first locking member 214 positioned on at least a portion thereof that engages body 230 (shown in FIG. 2b). As the operator advances shaft 210, first locking member 214 engages at least a portion of body passageway 232. First locking member 214 prevents an operator from retracting shaft 210 and prevents needle tip 301 from exiting from within the sheath 250. Alternatively or in addition, shaft 210 may be advanced further so that needle tip 301 retracts further within sheath 250. Preferably, shaft 210 has a horizontal dimension sized so that needle tip 301 is positioned within sheath 250 when first locking member 214 engages body 230.

Referring to FIG. 2a, needle sheath 250 is constructed as part of, or attaches to, shaft 210. Sheath 250 is preferably a tubular member having a passageway 251 extending therethrough which has a horizontal dimension sized so that needle tip 301 is positioned within passageway 251 when first locking member 214 engages body 230.

Sheath 250 is positioned so that as shaft 210 is advanced, sheath 250 moves over needle tip 301. When first locking member 214 engages body 230, needle tip 301 is positioned completely within passageway 251 to prevent accidental punctures to operators.

Sheath 250 is sized and positioned on shaft 210 so that needle tip 301 is positioned within sheath 250 when first locking member 214 engages body 230 and when needle tip 301 is withdrawn completely from catheter 200. Sheath 250 is positioned on shaft 210 a sufficient distance from body 230 so that needle tip 301 is positioned within sheath 250 when first locking member 214 engages body 230.

First locking member 214 and sheath 250 are positioned along the horizontal axis of shaft 210 so that when first locking member 214 engages body 230, sheath 250 slides over needle tip 301.

FIG. 2b illustrates body 230 having a passageway 232 that allows shaft 210 to slidably engage body 230. Passageway 232 is preferably a bore extending horizontally through body 230 along the same axis as needle 300. In other embodiments not shown, body 230 may be configured with a slot along an exterior surface of body 230 or other suitable configuration that allows shaft 210 to slidably engage body 230 and operate substantially as described herein.

Body 230 also has a pair of finger grips 231 to assist operators in gripping insertion device 340. A body fluid collection chamber 233 attaches to or is constructed as part of body 230. Chamber 233 has a fluid inlet 234 attachable to al fluid outlet in needle head 320 (see FIG. 4). Chamber 233 also has a fluid outlet 235 that comprises a connector 236 that allows chamber 233 to connect to tubing or other devices. Fluid inlet 234 is constructed so that needle head 320 will slide onto and fluidly and sealingly connect to chamber 234. Body 230 engages needle 300 relative to hold it in place.

Backflow tubing 237 removably attaches to or is constructed as part of chamber 233 as shown in FIGS. 2b, and 3a–3c (in FIGS. 7, 8a–8c in embodiments described later). Backflow tubing 237 has a closeable or closed end, such as connector 236, and allows extended viewing of fluid flow through backflow tubing 237, insuring proper needle tip placement in the patient's blood vessel. As long an operator views fluid flowing into backflow tubing 237, the operator knows that catheter tip 201 is positioned intravenously.

Backflow tubing 237 can be of various sizes and lengths, preferably at least 1 cubic centimeter (cc), more preferably about 3 cc. The exact size and volume of backflow tubing 237 will depend on the user's desires, but backflow tubing 237 should be of sufficient length to allow a user multiple attempts at catheterization so that extra volume exists within backflow tubing 237 for the extra blood flow that will occur with more than one attempt at properly inserting the catheter in the blood vessel. Backflow tubing 237 may be used with any of the embodiments described herein.

Medical personnel may use conventional needles 300 with the present invention. Viewing FIG. 4, needles 300 generally comprise a hollow shaft 322 extending between needle tip 301 and needle head 320 so that fluid may flow from tip 301 through shaft 322 and into needle head 320. Needle head 320 may also comprise a fluid chamber 321 as shown. Needle 300 slidingly inserts within catheter 200 so that only needle tip 301 protrudes through catheter tip 201 when insertion device 340 inserts within vessel 100 as shown in FIG. 5a.

Figure 4:
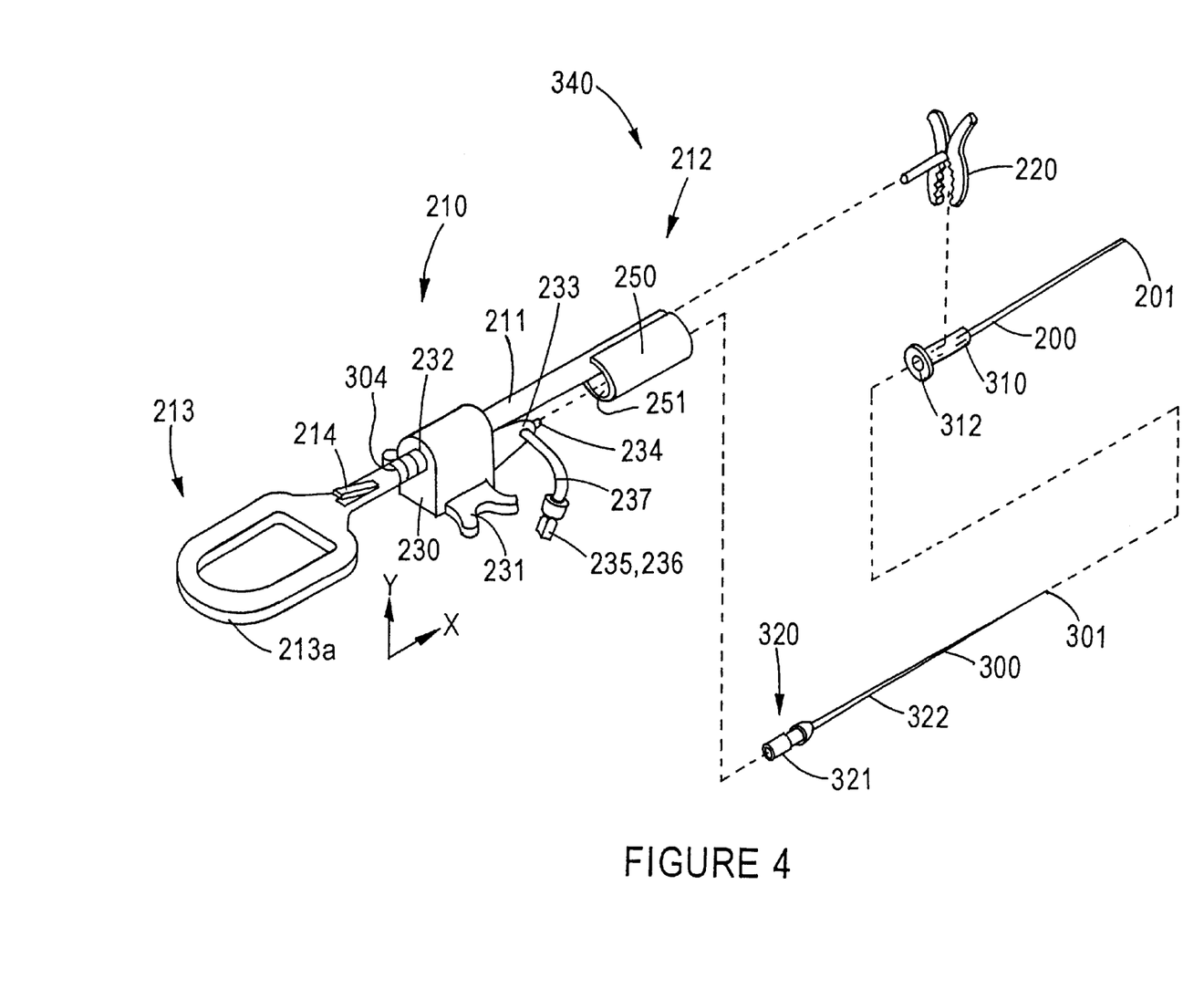
FIG. 4 illustrates an exploded view of the catheter insertion device shown in FIGS. 3a–3b.
Figure 5A:
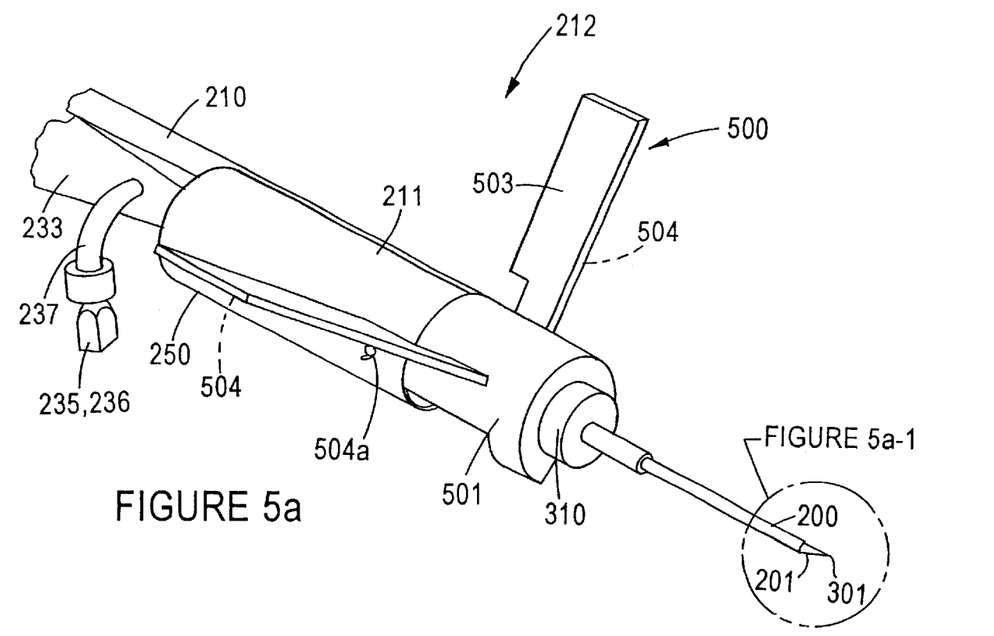
Figure 5A:
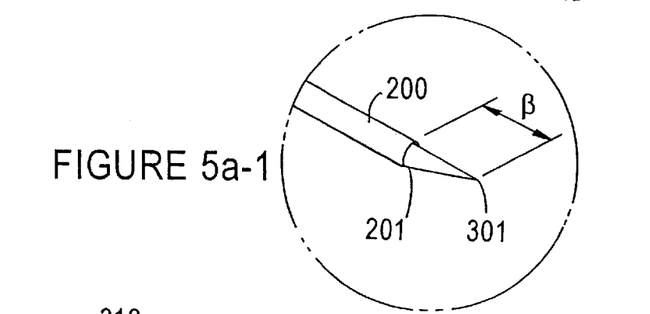

Viewing FIG. 4, in operation, with shaft 210 fully retracted, the operator sealing attaches needle 300 to body fluid inlet 234 via needle head 320. Needle 300 inserts coaxially through catheter 200 until needle tip 301 protrudes through catheter tip 201. Clip 220 (or clip 501) grips catheter 200 and releasably attaches to catheter end 212 of shaft 210. A lip 312 prevents clip 220 from disengaging catheter 200, although adhesive material or other attachment means may be used to ensure that catheter 200 remains attached to clip 220.

An operator prepares skin 110 surrounding the insertion point with an antibacterial agent. With one hand, the operator locates vessel 100 to be catheterized and holds skin 110 and vessel 100 in a fixed position to prevent vessel 100 from moving when punctured. With the other hand, the operator advances insertion device 340 by inserting and pushing needle tip 301 and catheter tip 201 through skin 110 and advances them until needle tip 301 enters vessel lumen 120. The operator observes that needle tip 301 enters vessel 100 by observing fluid entering needle fluid chamber 321 and backflow tubing 237.

Figures 3A, 3B, 3C:
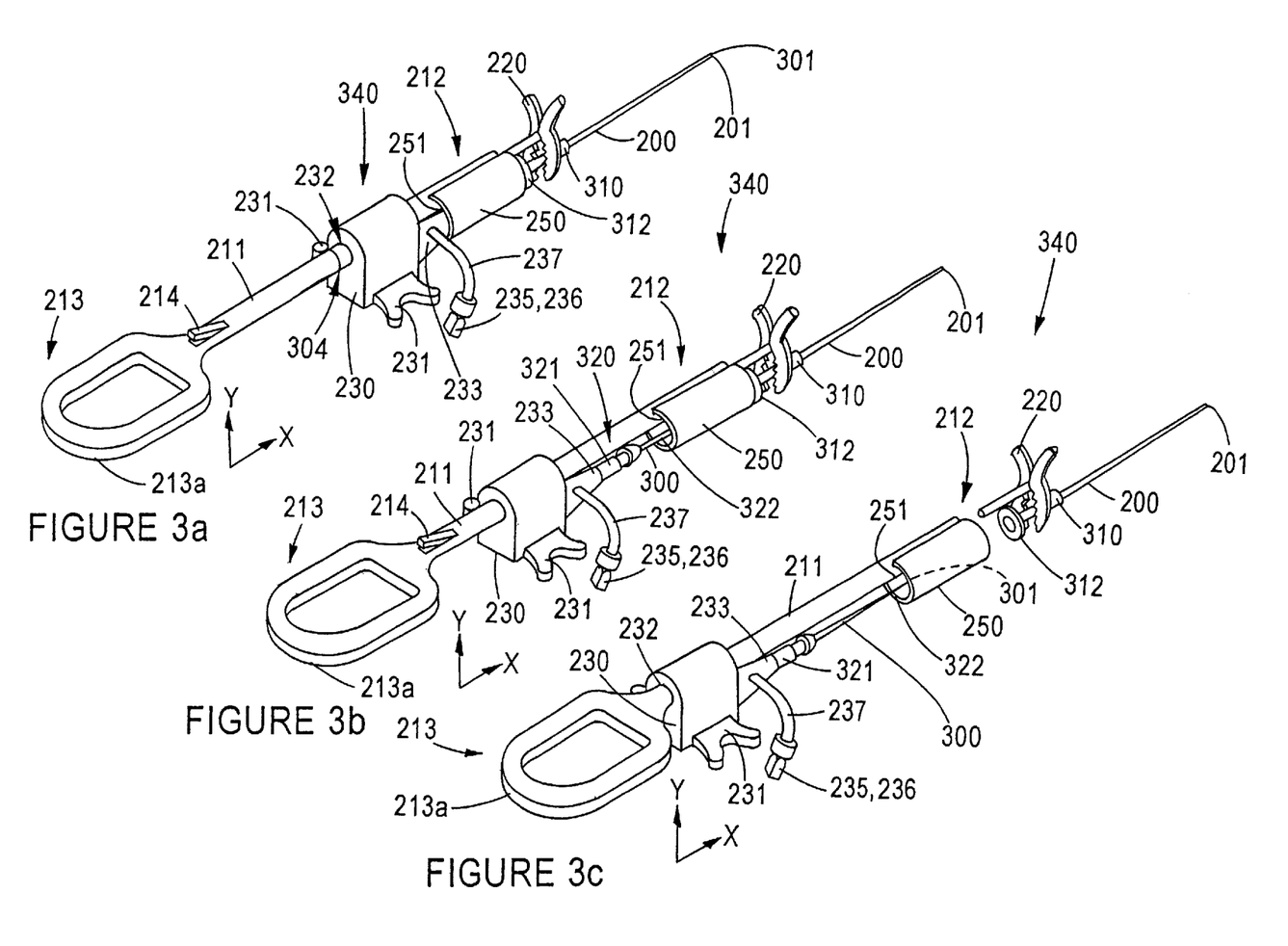
FIG. 3a illustrates an embodiment of a catheter insertion device ready for insertion into a vessel.
FIG. 3b illustrates an embodiment of a catheter insertion device where the shaft has been partially advanced.
FIG. 3c illustrates an embodiment of a catheter insertion device with the catheter released from the device.

Viewing FIGS. 3a–3c, while blood enters needle head chamber 321 and body fluid chamber 233, the operator's thumb advances shaft 210 as the index and middle fingers hold finger grips 231 just as the operator would use an ordinary syringe. A gauge indicator 304 on shaft 210 indicates the safe distance that catheter tip 201 may insert within vessel 100 before withdrawing needle 300 without causing a misstart. Gauge indicators 304 may comprise visible lines configured around the diameter of shaft 210 or other devices as described herein.

As shown in the blown up portion of FIG. 5a, there is a distance between needle tip 301 and catheter tip 201, referred to herein as the tip distance and marked as β, that exists between tips 201, 301 when the needle-catheter combination is ready for insertion into a blood vessel. The tip distance also equals the relative distance that the shaft may be advanced before needle tip 301 retracts completely within catheter 200 and past catheter tip 201.

After needle tip 301 has retracted within catheter 200 and past catheter tip 201, the operator should preferably not reinsert catheter 200. If catheter 200 is reused, needle tip 301 could shear off portions of catheter 200 and catheter tip 201 during reinsertion.

Figure 9A:
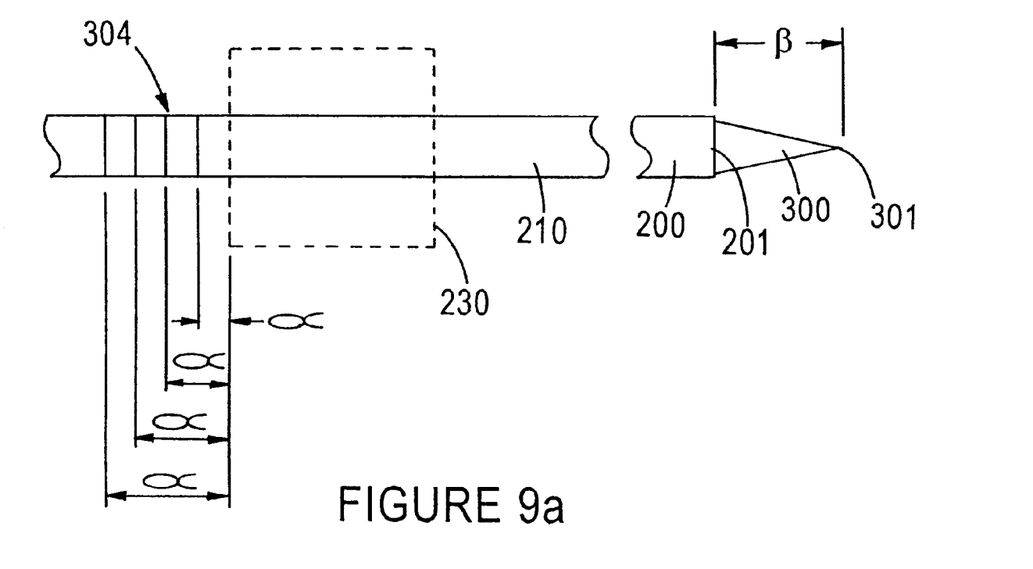
FIGS. 9a and 9b illustrate the positioning of the gauge indicators on the shaft relative to the insertion device body.
Figure 9B:
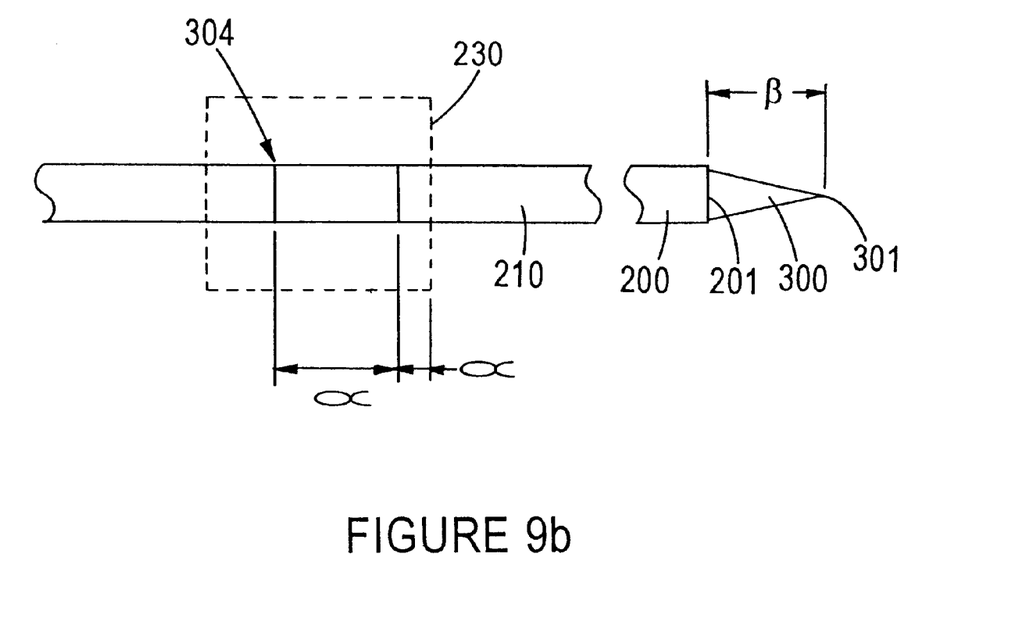

Gauge indicator 304 is positioned a distance, referred to as safe distance α, from an end of body 230 as shown in FIGS. 9a and 9b so that the operator knows the distance that the shaft can be advanced without requiring the original catheter 200 and needle 300 to be discarded.

In the embodiment shown in FIG. 9a, gauge indicators 304 are positioned exterior of body 230 when device 340 is ready to insert catheter 200 so that if gauge indicator 304 substantially enters body 230, the operator will know he has exceeded safe distance α and will require a new catheter 200 and needle 300 if reinsertion is necessary.

Another embodiment is shown in FIG. 9b. Gauge indicator 304 is positioned along shaft 210 within body 230 when device 340 is ready to insert catheter 200 so that if gauge indicator 304 substantially exits body 230, the operator will know he has exceeded safe distance α and will require a new catheter 200 and needle 300 if reinsertion is necessary.

In other embodiments, gauge indicators 304 may comprise slightly raised annular rings positioned around shaft 210. When safe distance α has been exceeded, the operator will feel a slight "bump" as appropriate gauge indicator 304 engages body 230, informing the operator that needle 300 and catheter 200 must be replaced. The operator must restart the insertion process. As long as the operator does not feel the bump, the operator may continue the insertion process.

Alternatively, gauge indicators 304 may be configured as second locking mechanisms so that if safe distance α is exceeded, needle tip 301 will be "locked" and prevented from extending from catheter tip 201 by retraction of shaft 210. Each gauge indicator 304 may be configured as a separate detent or locking mechanism in embodiments with multiple gauge indicators 304 (see FIG. 9a).

Because insertion device 340 may interchangeably work with different sized needles 300 and catheters 200, multiple gauge indicators 304 may be positioned along shaft 210 as shown in FIG. 9a to accommodate changes in tip distance β (and safe distance α accordingly) resulting from the use of larger or smaller needles 300 and catheters 200.

"Advance" and derivatives thereof, when referring to the movement of shaft 210 means the relative movement between needle 300 and shaft 210 along the horizontal axis, whereby shaft 210 moves horizontally such that first locking member 214 advances toward body 230 and sheath 250 advances toward needle tip 301. Alternatively and in addition, one may view this relative movement as needle tip 301 retracting within sheath 250.

First locking member 214 engages body 230 so that shaft 210 may be advanced to further retract needle tip 301 within sheath 250, but shaft 210 may not retract. Although first locking member 214 is shown positioned on shaft 210, shaft 210 and body 230 may be configured in a variety of other ways as long as shaft 210 and body 230 "lock" to accomplish the purposes described herein.

After the operator has positioned catheter 200 within vessel 100, the operator advances shaft 210 until catheter 200 is properly positioned in vessel 100. Then, while preferably holding shaft 210 in place, the operator retracts body 230 to retract needle tip 301 from within vessel 100 and into sheath 250. The operator then uses first locking member 214 to lock body 230 and shaft 210. First locking member 214 preferably engages body 230 so that it fixes the position of shaft 210 so that shaft 210 does not cause needle tip 301 to protrude from sheath 250. Viewing FIG. 3c, after the operator locks shaft 210 within body 230 (locking needle tip 301 within sheath 250), the operator releases clip 220 (or clip 501 or clip 750) from shaft 210. Catheter 200 is ready for attachment to medication tubing, monitoring equipment, etc.

The configuration of the embodiments of the present invention allow an operator to use a single hand to operate catheter insertion device 340 and thus decrease the number of misstarts.

Figure 5B:
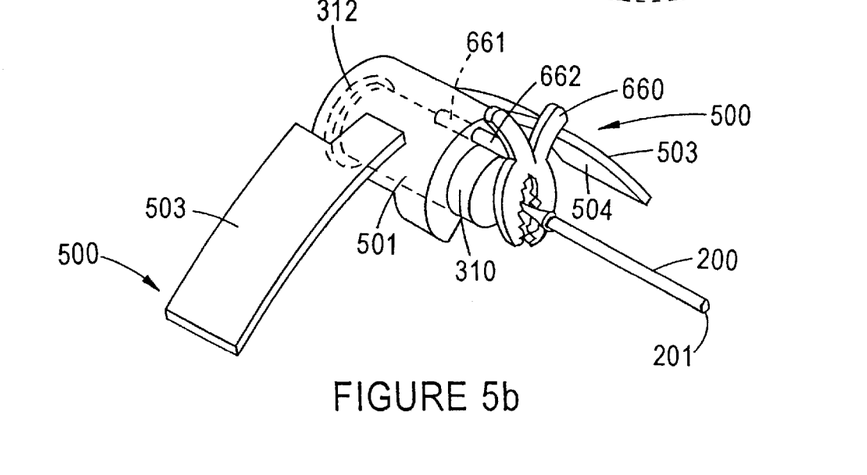
FIG. 5b illustrates the use of a clamp to seal the catheter after it has been inserted within a vessel.

Viewing FIGS. 5a and 5b, after the operator positions catheter 200 within vessel 100, the operator may position catheter 200 relative to skin 110 using a fastening member 500. In this embodiment, a clip 501 replaces clip 220. Clip 501 has an opening 502 therein that grips catheter 200 within opening 502 so that clip 501 grips and holds catheter 200. Opening 502 is sized and configured so that needle 300 may insert through catheter 200 as previously described. When clip 501 grips catheter 200, lip 312 preferably rests outside opening 502 as shown in FIG. 5b.

Figure 6:
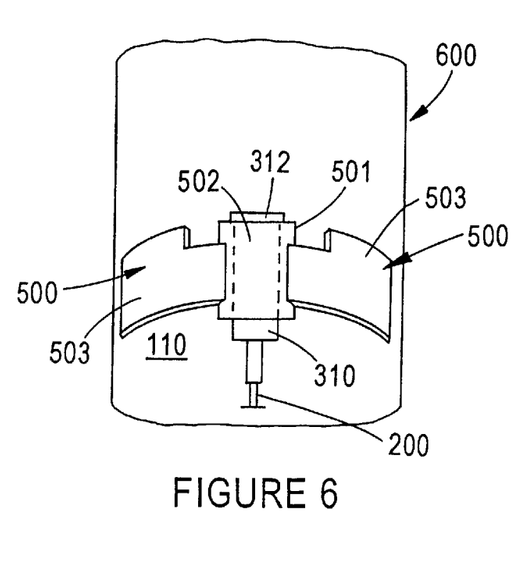
FIG. 6 illustrates a top view of the fastening member shown in FIGS. 5a and 5b attached to a patient's arm with the catheter inserted through the skin and to a vessel.

One or more adhesive wings 503 attach to clip 501 (shown in a raised position in FIG. 5a). Wings 503 have an adhesive side 504 that is covered by protective strips 504a. Viewing FIG. 6, after the operator properly positions catheter 200 within vessel 100, the operator folds wings 503 toward skin 110 on appendage 600. The operator removes protective strip 504a, exposing adhesive side 504. The operator positions adhesive sides 504 against skin 110 thereby fixing the position of catheter 200.

As shown in FIG. 5b, a clamp 660 may be positioned on catheter 200 to fluidly seal catheter 200 when catheter 200 has been inserted within a vessel. Clamp 660 prevents blood backflow from the catheterized vessel to the environment. Clamp 660 may be freely positionable or may mount onto clip 501 at bore 661 using clamp stem 662 which slidably engages bore 661 as shown in FIG. 5b (or onto clip 750 (not shown)). Although clamp 660 is shown in use with the present invention, it may be used in connection with other conventional catheters and catheter insertion devices. Clamp 660 is preferably configured so that it does not crush or deform catheter 200 when engaged therewith after needle 300 has been removed from within catheter 200 but configured so that it provides sufficient compression of hollow catheter 200 to seal it.

Figures 7, 7A:
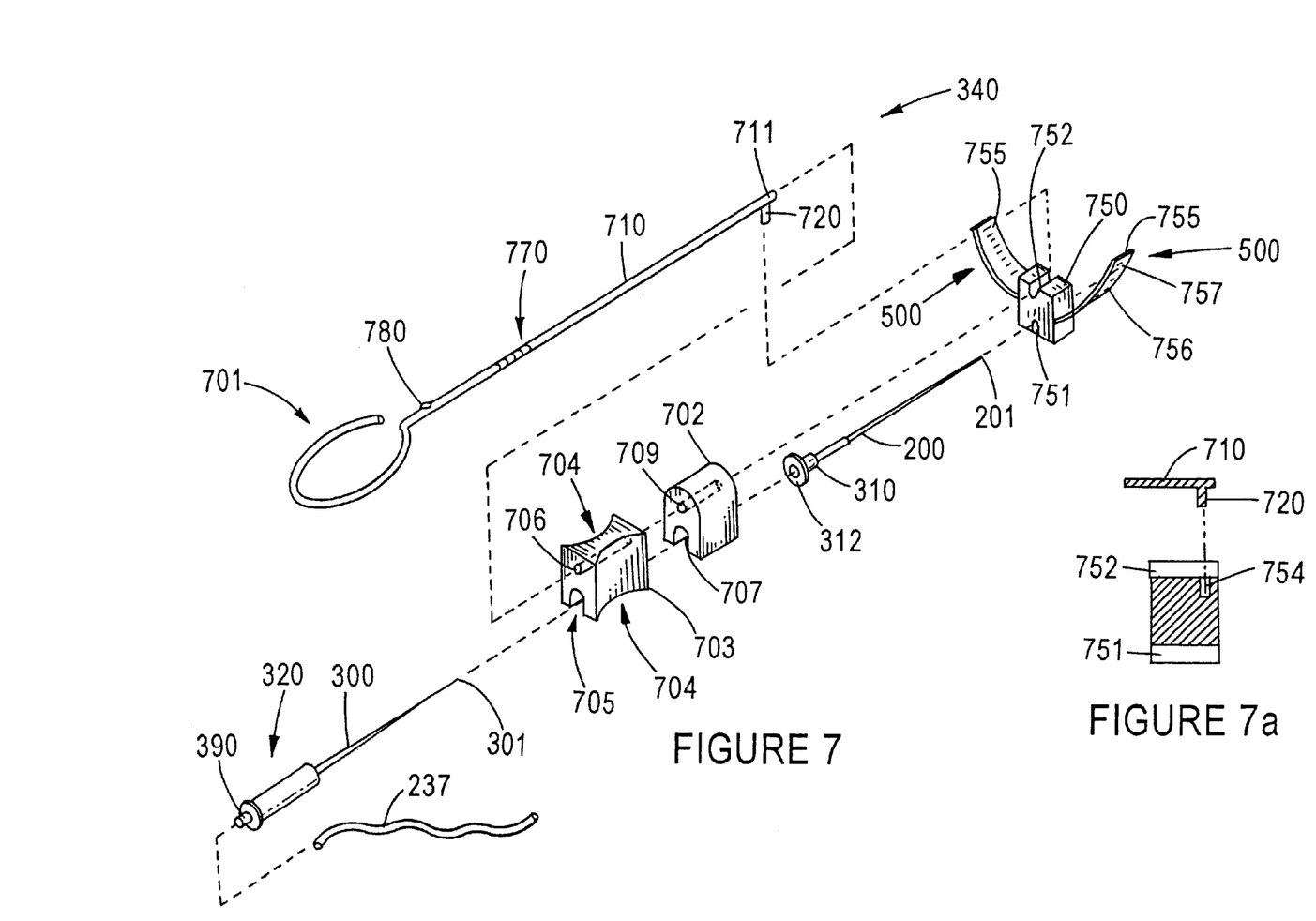
FIG. 7 illustrates an exploded view of an alternate embodiment of a catheter insertion device.
FIG. 7a illustrates a cross-sectional view of the shaft-clip engagement shown in FIG. 7.

Another embodiment of the present invention is shown in FIG. 7. Shaft 710 comprises a shaft having a catheter end 711 and a ring-shaped first end 701. Shaft 710 slidingly inserts through body 703 via bore 706 which extends horizontally through body 703. Body 703 is configured with a pair of indentations 704 along the sidewalls of body 703 to assist an operator in gripping body 703 much like finger grips 231 previously described. A U-shaped slot 705 extends along the bottom surface of body 703. Slot 705 is sized to allow needle head 320 to fit therein, preferably allowing needle head 320 to snap-fit within slot 705 so that needle 300 is fixedly positioned relative to body 703. Connector end 390 protrudes from body 703 so that needle head 320 may fluidly connect to backflow tubing 237 to provide an extended backflow chamber for blood during the insertion process as previously discussed.

Slot 705 may also be constructed as a bore extending horizontally through body 703. If a bore construction is used, the bore must be configured to allow needle 300 to be inserted therethrough while at the same time fixing the position of needle 300 relative to body 703 or allow needle 300 to engage body 703 as shown.

As discussed in previous embodiments, a locking member 780 is preferably positioned near first end 701 so that shaft 710 lockably engages body 703 when needle tip 301 has fully retracted with slot 707 of sheath 702. Sheath 702 has a horizontal dimension sized so that needle tip 301 is positioned within slot 707 when locking member 780 engages body 703. Sheath 702 is positioned so that as shaft 710 is advanced, sheath 702 slides over needle tip 301. When locking member 780 engages body 703, needle tip 301 is positioned completely within slot 707 to prevent accidental punctures to operators. Sheath 702 is sized and positioned on shaft 710 so that needle tip 301 is positioned within sheath 702 when locking member 780 engages body 703 and when needle tip 301 is withdrawn completely from catheter 200. Sheath 702 is positioned on shaft 710 a sufficient distance from body 703 so that needle tip 301 is positioned within sheath 702 when locking member 780 engages body 703.

Sheath 702 is also configured with a U-shaped slot 707 extending along its bottom edge. Sheath 702 has a first bore 709 that allows catheter end 711 of shaft 710 to insert therethrough, allowing shaft 210 to slidably engage sheath 702. First bore 709 is configured so that sheath 702, though slidingly positionable on shaft 710, is removably attached thereto when insertion device 340 is in use.

Slot 707 may also be constructed as a bore extending horizontally through sheath 750. If a bore configuration is used, the bore is preferably configured to align with slot 751 in clip 750 to allow catheter lip 312 to be positioned within slot 707 so that needle tip 301 is not exposed after it has been removed from within catheter 200.

Clip 750 has slots 751, 752 configured along its upper and lower ends. Slot 707 allows catheter 200 to snap into slot 751. Slot 752 is configured to receive catheter end 711 of shaft 710. Viewing FIG. 7a, a hole 754 is configured within clip 750 to receive shaft stem 720, which snaps into hole 754 so that shaft 710 releasably attaches to clip 750 during operation of catheter insertion device 340. Although clip 750 is shown with slots 751, 752, other configurations may be used for clip 750 to allow clip 750 to reasonably engage both catheter 200 and shaft 710.

Figures 8A, 8B, 8C:
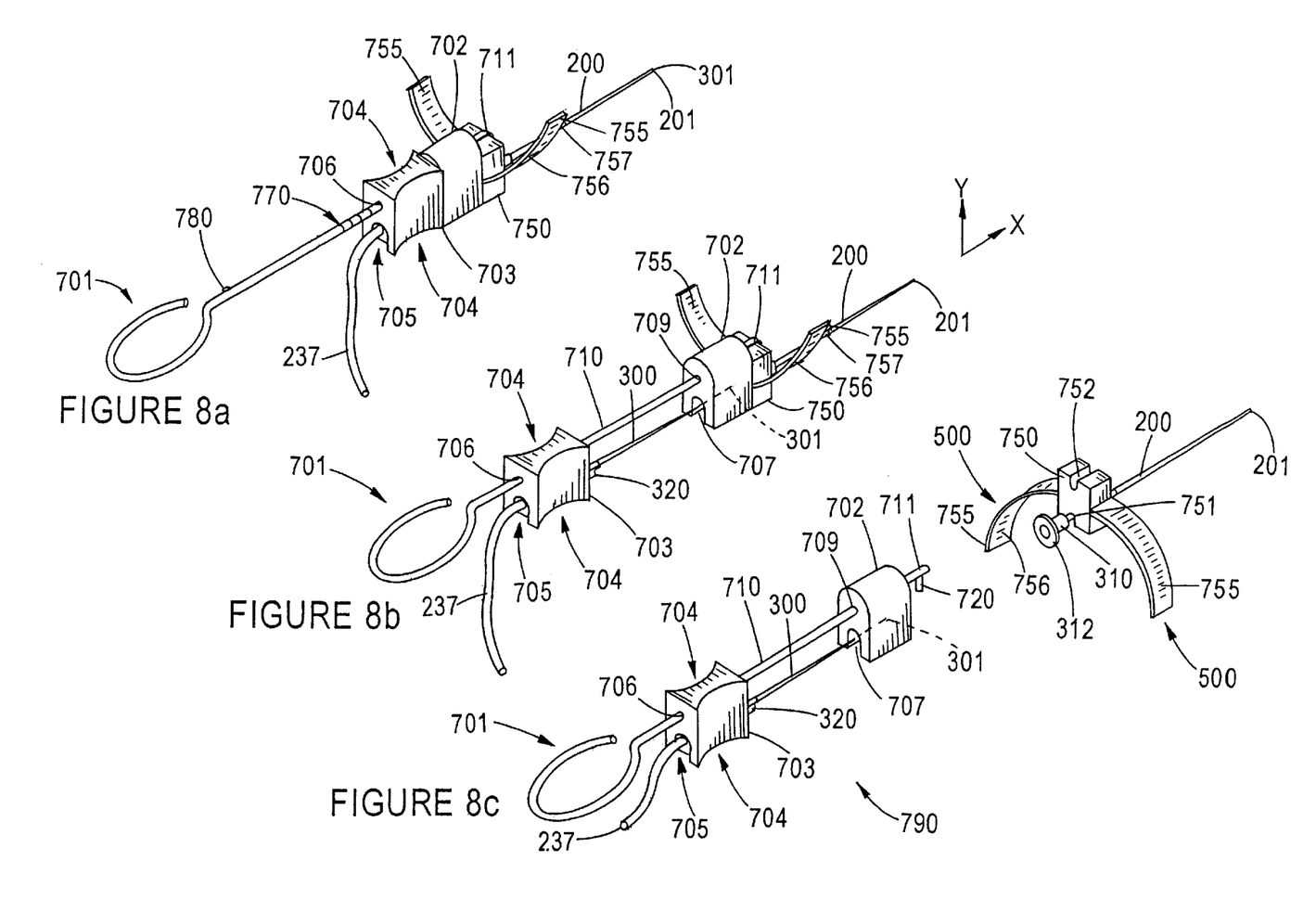
FIG. 8a illustrates an embodiment of the catheter insertion device shown in FIG. 7 ready for insertion into a vessel.
FIG. 8b illustrates the embodiment of the catheter insertion device shown in FIG. 7 where the shaft has been partially advanced.
FIG. 8c illustrates the embodiment of the catheter insertion device shown in FIG. 7 with the catheter released from the device.

FIG. 8a illustrates insertion device 340 ready for deployment of catheter 200 within a vessel 100 with needle tip 301 protruding through catheter tip 201. FIG. 8b illustrates the positioning of the components of first component 790 when locking member 780 has engaged body 703, thereby locking shaft 710 and body 703. Needle tip 301 is shown positioned within sheath 702. FIG. 8c illustrates clip 750 gripping catheter 200 and detached from first component 790, so that first component 790 can be properly disposed. Fastening member 500 can also be incorporated into this embodiment arid comprises wings 755 attached to clip 750, which are shown folded down ready for fastening to a patient's skin.

One or more adhesive wings 755 attach to clip 750 (shown in a raised position in FIGS. 8a and 8b). Wings 755 have an adhesive side 756 that is covered by protective strips 757.

The embodiment shown in FIGS. 7 and 8a–8c operates as follows. An operator prepares skin 110 surrounding the insertion point with an antibacterial agent. The operator removes protective strip(s) 757, exposing adhesive side(s) 756. With one hand, the operator locates vessel 100 to be catheterized and holds skin 110 and vessel 100 in a fixed position to prevent vessel 100 from moving when punctured. With the other hand, the operator advances the device 340 by inserting and pushing needle tip 301 and catheter tip 201 through skin 110 and advances them until needle tip 301 enters vessel lumen 120. The operator observes that needle tip 301 enters vessel 100 by observing fluid entering needle head chamber 321 and/or tubing connected at connector end 390. While blood enters needle head chamber 321, the operator's thumb advances shaft 710 as the index and middle fingers hold indentations 704 similar to how an operator would use an ordinary syringe. One or more gauge indicators 770 may be positioned on shaft 710 and operate as previously discussed.

After the operator has positioned catheter 200 within vessel 100, the operator advances shaft 710 until catheter 200 is properly inserted within vessel 100. Then, while preferably holding shaft 710 in place, the operator retracts body 703 to retract needle tip 301 from within vessel 100 and into sheath 702. The operator then uses locking member 780 to lock body 703 and shaft 710. Locking member 780 preferably engages body 703 so that it fixes the position of shaft 710 so that shaft 710 does not cause needle tip 301 to protrude from sheath 702. After the operator locks shaft 710 within body 703 (locking needle tip 301 within slot 707 of sheath 702), the operator releases clip 750 from shaft 710. Catheter 200 is ready for attachment to medication tubing, monitoring equipment, etc.

Viewing FIG. 8c, after the operator properly positions catheter 200 within vessel 100, the operator removes protective strips 757 and folds wings 755 downward to position catheter 200. Shaft 710 is then released from clip 750 by removing stem 720 from within hole 754 in clip 750 (see FIG. 7a). The operator positions adhesive sides 504 against skin 110 thereby fixing the position of catheter 200 relative to vessel 100.

Although the preferred embodiment has been described, it will be appreciated by those skilled in the art to which the present invention pertains that modifications, changes, and improvements may be made without departing from the spirit of the invention defined by the claims.

What is claimed is:

1. A catheter insertion device comprising:
    a. a shaft having a first end and a catheter end, said catheter end configured to releasably engage a hollow catheter having a tip;
    b. a sheath positioned on said shaft, said sheath configured to have a passage therethrough, said sheath positioned to align said passage with said catheter;
    c. a body slidably positioned on said shaft, said body attachable to a needle and configured to align a needle with said passage of said sheath and with said catheter;
      wherein a needle, said sheath, said shaft and said catheter are sized and spaced to position a needle tip of a needle beyond said catheter tip when said body is advanced toward said catheter end of said shaft and to remove the needle tip from within said catheter and to position the needle tip within said passage of said sheath when said body is retracted toward said first end of said shaft.

2. A device according to claim 1 wherein said shaft further comprises a clip attaching said catheter to said shaft.

3. A device according to claim 2 wherein said clip is engageable with said sheath.

4. A device according to claim 2 wherein said clip is engageable with said shaft.

5. A device according to claim 2 wherein said clip is configured to fluidly seal said catheter when a needle positioned within said catheter has been removed therefrom.

6. A device according to claim 2 further comprising a clamp configured to fluidly seal said catheter when a needle positioned within said catheter has been removed therefrom.

7. A device according to claim 2 wherein said body comprises a shaft bore extending therethrough, said shaft slidably engaging said body via said shaft bore.

8. A device according to claim 2 wherein said body has exterior surface, said body comprising at least one slot configured along said exterior surface, said slot adapted to allow said shaft to movably engage said body.

9. A device according to claim 7 wherein said body comprises a fluid chamber comprising a fluid inlet and a fluid outlet, said fluid inlet connectable to said needle.

10. A device according to claim 1 further comprising at least one fastening member configured to substantially fix the position of said catheter.

11. A device according to claim 1 further comprising at least one locking member that prevents said needle tip from advancing from said sheath.

12. A device according to claim 1 wherein said sheath is sized so that said needle tip is positioned within said sheath when said locking member engages said body.

13. A device according to claim 1 further comprising a needle engageable with said body, said needle insertable through said passage in said sheath and insertable through said catheter.

14. A device according to claim 1 wherein said sheath is positioned so that the tip of said needle is positioned within said sheath when said needle tip is withdrawn from said catheter.

15. A device according to claim 1 wherein said shaft has a horizontal dimension sized so that said needle tip is positioned within said sheath when said locking member engages said body.

16. A device according to claim 10 wherein said fastening member comprises at least one section of adhesive material positioned on said catheter, said section adapted to adhere to a patient to substantially fix the position of said catheter.

17. A device according to claim 16 wherein said fastening member comprises at least one section of adhesive material positioned on said clip, said section adapted to adhere to a patient to substantially fix the position of said catheter.

18. A device according to claim 1 further comprising a backflow chamber.

19. A device according to claim 18 wherein said backflow chamber has a volume of at least 1 cc.

20. A device according to claim 1 further comprising at least one gauge indicator positioned on said shaft.

21. A device according to claim 20 wherein said gauge indicator comprises one or more annular rings positioned around said shaft.

22. A method for intravenous insertion of a catheter using a catheter insertion device comprising:
   a. a shaft having a first end and a catheter end, said catheter end configured to releasably engage a hollow catheter having a tip;
   b. a sheath positioned on said shaft, said sheath configured to have a passage therethrough, said sheath positioned to align said passage with said catheter;
   c. a body slidably positioned on said shaft, said body attachable to a needle and configured to align a needle with said passage of said sheath and with said catheter;

wherein a needle, said sheath, said shaft and said catheter are sized and spaced to position a needle tip of a needle beyond said catheter tip when said body is advanced toward said catheter end of said shaft and to remove the needle tip from within said catheter and to position the needle tip within said passage of said sheath when said body is retracted toward said first end of said shaft;

said method comprising the steps of
   i. grasping the skin of said patient with one hand in the area of desired catheterization to fix the position of said skin and surrounding tissue relative to a vessel to be catheterized;
   ii. holding in the other hand said catheter insertion device;
   iii. inserting said needle and said catheter into said vessel until fluid flows from said vessel through said needle; and,
   iv. advancing said catheter into said vessel to a desired position.

23. A method according to claim 22 further comprising the step of retracting said body until said needle tip is covered by said sheath.

24. A method according to claim 23 further comprising the step of releasing said catheter from said shaft.

25. A method according to claim 24 further comprising the step of fastening said catheter with a fastening member.

* * * * *